United States Patent
Rueller et al.

(10) Patent No.: US 9,636,472 B2
(45) Date of Patent: May 2, 2017

(54) VENTILATION METHOD AND VENTILATION DEVICE

(75) Inventors: Stephan Rueller, Bargteheide (DE); Susanne Greve, Hamburg (DE)

(73) Assignee: Forschungszentrum Borstel Liebniz-Zentrum fuer Medizin und Biowissenschaften, Borstel (DE)

( * ) Notice: Subject to any disclaimer, the term of this patent is extended or adjusted under 35 U.S.C. 154(b) by 952 days.

(21) Appl. No.: 13/581,947

(22) PCT Filed: Feb. 18, 2011

(86) PCT No.: PCT/EP2011/000781
§ 371 (c)(1),
(2), (4) Date: Aug. 30, 2012

(87) PCT Pub. No.: WO2011/107219
PCT Pub. Date: Sep. 9, 2011

(65) Prior Publication Data
US 2012/0318268 A1    Dec. 20, 2012

Related U.S. Application Data

(60) Provisional application No. 61/310,060, filed on Mar. 3, 2010.

(30) Foreign Application Priority Data

Mar. 3, 2010 (DE) .................. 10 2010 010 248

(51) Int. Cl.
*A61M 16/00* (2006.01)
*A61M 16/20* (2006.01)

(52) U.S. Cl.
CPC ........ *A61M 16/00* (2013.01); *A61M 16/0069* (2014.02); *A61M 16/201* (2014.02);
(Continued)

(58) Field of Classification Search
CPC .............. A61M 16/00; A61M 16/0069; A61M 16/201; A61M 2016/0021;
(Continued)

(56) References Cited

U.S. PATENT DOCUMENTS 5,752,509 A * 5/1998 Lachmann et al. ...... 128/204.23
5,931,162 A * 8/1999 Christian ................. 128/204.23
(Continued)

FOREIGN PATENT DOCUMENTS

EP        1820526 A1    8/2007
WO       01/74430      10/2001

*Primary Examiner* — Justine Yu
*Assistant Examiner* — Douglas Sul
(74) *Attorney, Agent, or Firm* — Whitman, Curtis & Cook, P.C.

(57) ABSTRACT

The present invention relates to a method for the ventilation of a living being (3), the respiration airflow (v) flowing into the living being (3) and out of the living being (3) being detected, it being ascertained from the detected respiration airflow (v) whether an inhalation phase or an exhalation phase is present, and the air pressure (p) in a respiratory organ of the living being (3) being regulated, characterized in that, upon recognition of an inhalation phase, the air pressure (p) in the respiratory organ is raised at the beginning of the inhalation phase and lowered again with progressing respiration cycle.

27 Claims, 5 Drawing Sheets

(52) U.S. Cl.
CPC ............... *A61M 2016/0021* (2013.01); *A61M 2016/0027* (2013.01); *A61M 2016/0039* (2013.01)

(58) Field of Classification Search
CPC .. A61M 2016/0027; A61M 2016/0039; A61M 2230/42
USPC .................................................. 128/204.21
See application file for complete search history.

(56) References Cited

U.S. PATENT DOCUMENTS

| | | | |
|---|---|---|---|
| 6,105,575 A * | 8/2000 | Estes et al. .............. | 128/204.23 |
| 6,371,113 B1 * | 4/2002 | Tobia et al. .............. | 128/204.23 |
| 6,564,798 B1 * | 5/2003 | Jalde ........................ | 128/205.24 |
| 6,588,422 B1 * | 7/2003 | Berthon-Jones et al. ........................ | 128/204.23 |
| 6,626,175 B2 * | 9/2003 | Jafari .................... | A61M 16/00 128/204.18 |
| 7,152,598 B2 * | 12/2006 | Morris .................. | A61M 16/00 128/204.18 |
| 7,367,337 B2 * | 5/2008 | Berthon-Jones et al. ........................ | 128/204.18 |
| 2006/0000475 A1 * | 1/2006 | Matthews et al. ....... | 128/204.21 |
| 2006/0084877 A1 | 4/2006 | Ujhazy et al. | |
| 2008/0178880 A1 * | 7/2008 | Christopher ...... | A61M 16/0051 128/204.23 |

* cited by examiner

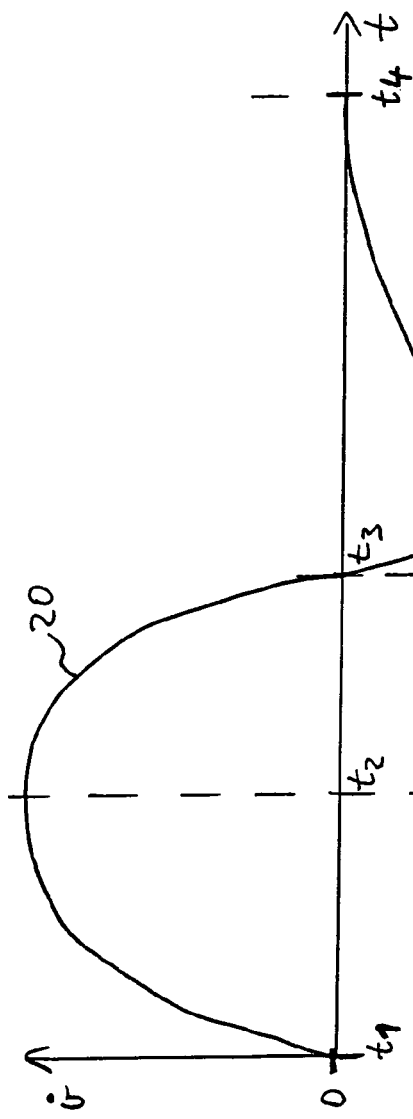
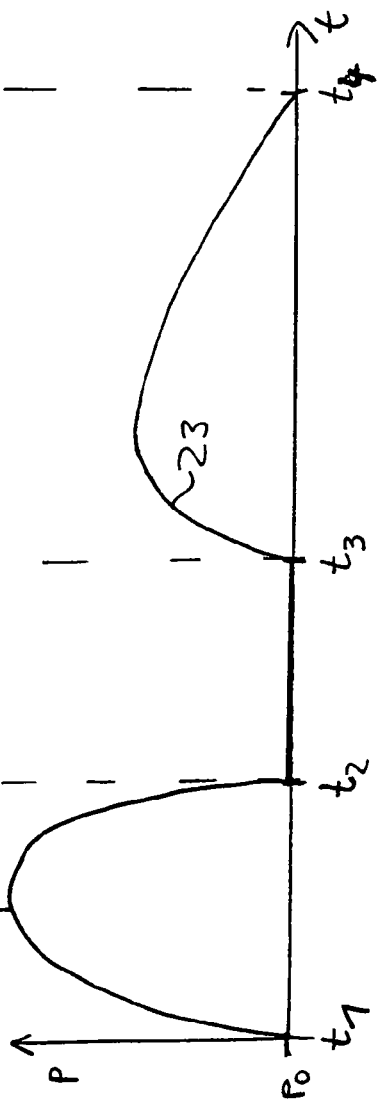
Fig. 2a
Fig. 2b

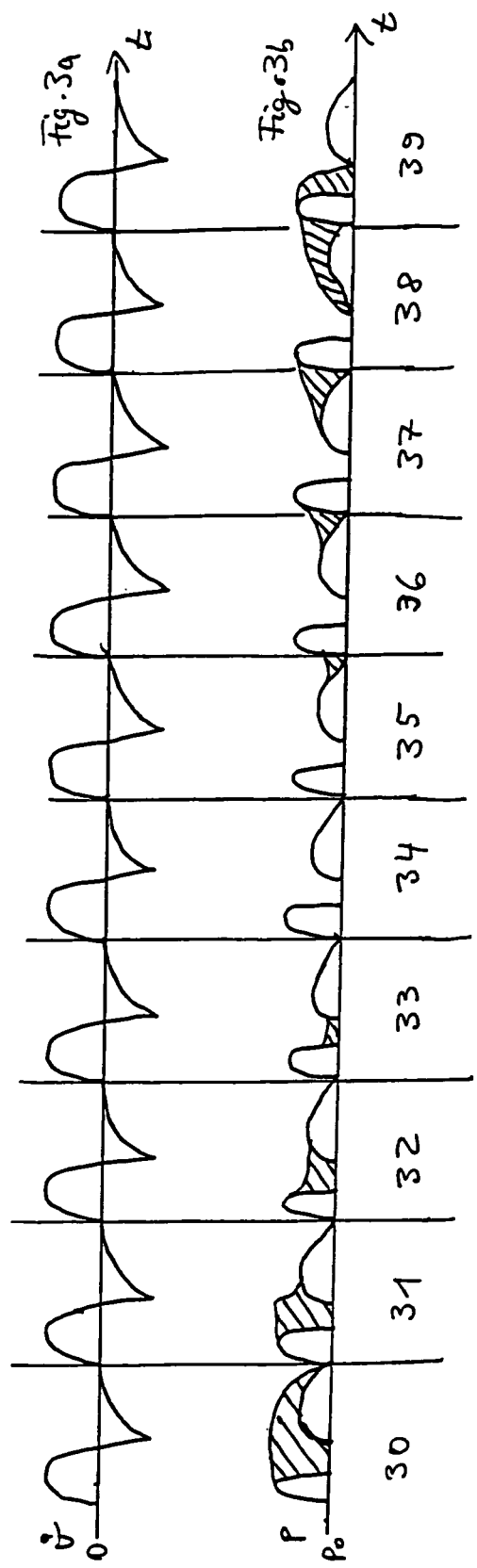

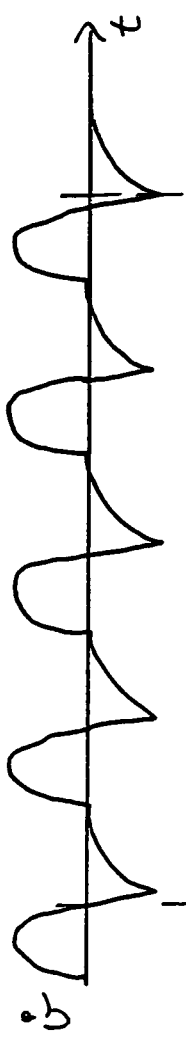
Fig. 4a
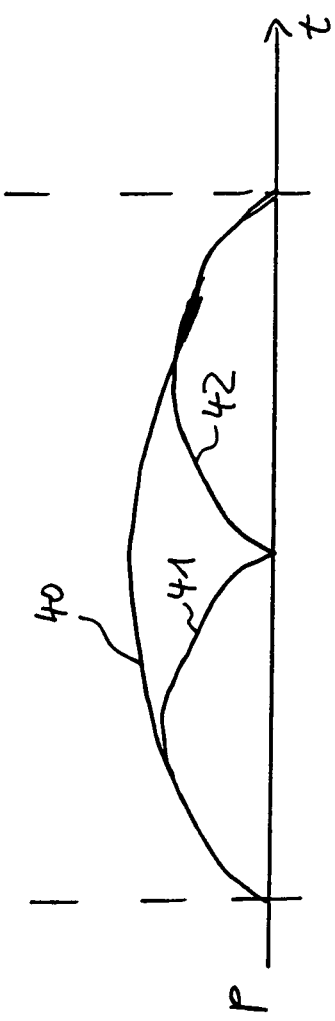
Fig. 4b
Fig. 4

VENTILATION METHOD AND VENTILATION DEVICE

CROSS-REFERENCE TO RELATED APPLICATIONS

This application is a 371 of International Application PCT/EP2011/000781 filed Feb. 18, 2011, which claims benefit to U.S Provisional Application 61/310,060 filed Mar. 3, 2010, both of which are incorporated herein by reference.

DESCRIPTION

BACKGROUND OF THE INVENTION

Field of the Invention

The invention relates to a method for the ventilation of a living being. Furthermore, the invention relates to a ventilation device having at least one controllable air delivery unit, at least one airflow meter, at least one pressure sensor, and having at least one programmable control unit and a valve control device having at least one pressure control valve, at least one airflow meter, at least one pressure sensor, and having at least one programmable control unit.

Background Description

In general, the invention relates to the field of the ventilation of patients having respiratory problems. COPD (Chronic Obstructive Pulmonary Disease) patients are cited as an example, especially those having hypercapnic respiratory insufficiency. In these patients, structural changes have occurred in the lungs because of various illnesses, which require increased work of the respiratory musculature in order to ensure sufficient gas exchange. As the illness progresses, the respiratory musculature is increasingly exhausted, as a result of which shortness of breath feelings can occur during respiration even upon very slight exertion. In pronounced cases, the respiratory musculature and the respiratory drive, in particular even at night while asleep, is no longer capable of compensating for the structural changes of the lungs by increased respiratory depth and increase of the respiratory frequency.

Ventilation devices have been proposed for supporting such patients, for example, in U.S. Pat. Nos. 6,105,575 or 6,240,919 B1. In such devices, it is provided that an inspirational pressure controlled by the ventilation device is supplied to the patient via a ventilation mask during inhalation (Inspiratory Postive Airway Pressure or IPAP) and an expirational pressure controlled b$_y$ the ventilation device is supplied during exhalation (Expiratory Positive Airway Pressure or (EPAP). The ventilation devices adjust themselves automatically to the patient. A typical pressure support for IPAP is 10 to 30 mbar, for example,and is in the range from 4 to 10 mbar for EPAP. The prevailing opinion is that the pressure amplitude is to be as high as possible in the scope of acceptance of the patient, in order to ensure the best possible respiration support.

However, some studies in the ventilation of COPD patients have shown that an enlargement of the pressure amplitude, i.e., the difference between IPAP and EPAP, does not result in the desired relief of the respiratory musculature, but rather frequently results in increased hyperinflation of the lungs.

SUMMARY OF THE INVENTION

It is therefore the object of the invention to disclose a method for the ventilation of a living being and a ventilation device for this purpose, which avoids the undesired hyperinflation of the lungs in the best possible manner.

This object is achieved by the invention for the ventilation of a living being, the respiration airflow ($\dot{v}$)flowing into the living being and out of the living being being detected, it being ascertained from the detected respiration airflow ($\dot{v}$) whether an inhalation phase or an exhalation phase is present, and the air pressure (p) in a respiratory organ of the living being being regulated, wherein, upon recognition of an inhalation phase, the air pressure (p) in the respiratory organ is raised at the beginning of the inhalation phase and lowered again with progressing respiration cycle.

It has been recognized that the undesired hyperinflation of the lungs is caused in that the additional air pumped in by the ventilation device for support cannot be sufficiently exhaled again in the exhalation phase by the patient, so that increased residual air remains in the pulmonary alveoli. Specifically, typical ventilation devices supply the patient with an excess pressure to support the inhalation during the inhalation phase and reduce the pressure in the exhalation phase, to support the exhalation phase through a low exhalation resistance. However, in patients having severe pulmonary illness, this has the result that, on the one hand, air is increasingly pressed into the patient in the exhalation phase and, on the other hand, the small airways, which are damaged in any case, and their branches to the pulmonary alveoli constrict as a result of the pressure which is reduced by the ventilation device and sufficient exhalation, i.e., ventilation of the lungs, cannot occur.

This is counteracted according to the invention in that, on the one hand, in the inhalation phase a variable pressure curve, which is reduced early, is proposed. It is provided that upon recognition of an inhalation phase, the air pressure in the respiratory organ is raised at the beginning of the inhalation phase and reduced again as the respiration cycle progresses. In this context, a sequence of one inhalation phase and one exhalation phase is understood as the respiration cycle. According to an advantageous refinement of the invention, the air pressure in the respiratory organ is already reduced again with progressing inhalation phase. A reduction of the pressure therefore advantageously already occurs with progressing inhalation phase and not only entirely at the end of the inhalation phase, as in known devices. This is illustrated for exemplary purposes in the pressure curves 30 through 32 of FIG. 3.

According to the invention, the exhalation phase is supported in that, in the exhalation phase, the air pressure in the respiratory organ is regulated in accordance with the respiration airflow or parameters of the exhalation derived therefrom, so that the respiration airflow flowing out of the living being reaches a predetermined amount. Therefore, a predetermined pressure is not set, as in known ventilation devices, but rather the air pressure is dynamically regulated in accordance with the respiration airflow of the exhalation, so that as a result a specific exhalation air flow can be ensured. For this purpose, the air pressure can be raised or lowered on demand, a corresponding minimum pressure in the respiratory organs being able to be dynamically maintained as a changing counterpressure by the regulation of the air pressure in accordance with the respiration airflow, so that the small airways and their branches to the pulmonary alveoli are kept open. A specific dynamic resistance is thus provided during the exhalation, which is surprisingly perceived as pleasant and supportive by the patient. As a result, improved deaeration thus occurs and the undesired hyperinflation of the lungs is avoided. In particular, even a relatively short pressure pulse during the exhalation helps in regard to opening of the airways.

According to an advantageous refinement of the invention, it is provided both that upon the recognition of an inhalation phase, the air pressure in the respiratory organ is raised and also, after temporary reduction of the air pressure upon recognition of the exhalation phase, the air pressure in the respiratory organ is also raised. In this way, the deaeration and thus the deflation of the lungs are advantageously supported. For this purpose, both asymmetry of the pressure curve to the respiration airflow of the patient and also a dynamic change of the pressure in the individual respiration phases are advantageously provided. A dynamic change of the pressure in the individual respiration phases is particularly advantageous for this purpose, i.e., the air pressure is not kept constant for a relatively long time as in known ventilation devices.

According to an advantageous refinement of the invention, the air pressure is set so that the air pressure is above an initial value, which is set at the beginning of the inhalation phase as a starting value, at every point in time.

According to an advantageous refinement of the invention, the pressure curve of the air pressure is continuously dynamically regulated discordantly at the start and end points in time of the inhalation and exhalation phases of the living being. This dynamic response has great significance in pathophysiology and fundamentally differs from previous ventilation devices, which always have a plateau of the pressure curve.

According to an advantageous refinement of the invention, the air pressure in the respiratory organ is first raised and then lowered in the inhalation phase with continuously decreasing slope. The air pressure in the respiratory organ can advantageously be lowered in the inhalation phase to an initial value which was set at the beginning of the inhalation phase as the starting value, before the inhalation phase is at an end. A basal pressure level comes into consideration as the starting value in particular, which is advantageously selected so that it lies slightly below the intrinsic PEEP (Positive End Expiratory Pressure—pressure level at the end of the exhalation phase).

According to an advantageous refinement of the invention, the air pressure in the respiratory organ is first raised and then lowered in the inhalation phase with continuously decreasing slope of the respiratory airflow.

According to an advantageous refinement of the invention, the air pressure in the respiratory organ is lowered to the initial value in the inhalation phase when the maximum of the respiration airflow has been reached during the inhalation phase. This allows a relatively early reduction of the pressure in the inhalation phase, which also favors avoidance of hyperinflation.

According to an advantageous refinement of the invention, the air pressure in the respiratory organ is increased in the inhalation phase to an amount so that the respiration airflow decreases during a period of time after reaching the maximum value of the respiration airflow in the directly following time by an amount so that the reduction speed of the respiration airflow is as low as possible.

According to an advantageous refinement of the invention, the air pressure is increased in the respiratory organ in the exhalation phase up to a maximum pressure, which is reached at the end of the exhalation phase of the living being. This is shown, for example, in the pressure curves 37 and 38 of FIG. 3.

According to an advantageous refinement of the invention, the air pressure is increased in the respiratory organ in the exhalation phase up to a maximum pressure, which is reached before half of the duration of an average exhalation phase of the living being. In this way, the pressure curve in the exhalation phase can approximate a natural exhalation of a healthy living being.

According to an advantageous refinement of the invention, upon recognition of the exhalation phase, the air pressure in the respiratory organ is raised at the beginning of the exhalation phase. In this way, it can be ensured the airways are kept free right at the beginning of the exhalation phase, so that exhalation can occur particularly deeply and effectively.

According to advantageous refinements of the invention, adaptive self-learning functions are provided, which allow further improvements during the respiration support. According to an advantageous refinement, the tidal volume is ascertained from the detected respiratory airflow. The tidal volume can be determined during an inhalation phase indirectly from the quantity of the inhaled air or in an exhalation phase indirectly from the quantity of the exhaled air, or as a mean value or as a derived value of the parameters measurably changed by these quantities of air during one respiration cycle or multiple respiration cycles. The maximum value and/or the pressure level of the air pressure in the respiratory organ is increased in the exhalation phase or the pressure curve is adjusted if an increase of the tidal volume is established in preceding respiration cycles. Optimum relaxation of the respiratory organs can thus be achieved adaptively. If no increase of the tidal volume is established, the maximum value and/or the pressure level of the air pressure in the respiratory organ in the exhalation phase can be kept at the existing value or slightly reduced again.

According to an advantageous refinement of the invention, the respiration frequency is ascertained. The maximum value and/or the pressure level of the air pressure in the respiratory organ in the exhalation phase is increased or the pressure curve is adjusted if a reduction of the respiration frequency is established in the preceding respiration cycles. This is based on the finding that a reduction of the respiration frequency is an indicator of improved ventilation within certain limits. Respiration anxiety which possibly results through increase of the maximum value or the pressure level of the air pressure can also be detected in this way. If respiration anxiety is detected, the pressure increase can be limited or also reduced again.

According to an advantageous refinement of the invention, the time curve of the air pressure and/or the respiration airflow in the respiratory organ is monitored for occurrence of a superimposed oscillation having higher frequency than the respiration frequency. The superimposed oscillation can be viewed as an expression of an inhomogeneous exhalation upon increased internal PEEP. If the superimposed oscillation has become greater in regard to the frequency and/or less in regard to its amplitude through a prior increase of the air pressure in the exhalation phase, the exhalation and thus the deflation of the lungs have improved. If no further improvement of the exhalation is displayed in regard to the superimposed oscillation, there is no increase of the maximum value or the pressure level of the air pressure during the exhalation. A reduction of the maximum value or the pressure level of the air pressure can be performed instead.

The increase of the maximum value or the pressure level of the air pressure only occurs up to a preset limiting value, of course.

According to an advantageous refinement of the invention, the air pressure in the respiratory organ is lowered at the end of the exhalation phase, until the end of the exhalation phase is reached. The reduction can advantageously be performed until reaching an initial value of the air pressure, which was set as the starting value at the beginning of the inhalation phase.

According to an advantageous refinement of the invention, an intrinsic PEEP of the living being is ascertained from the detected respiratory airflow in connection with the expiratory pressure increase. An initial value of the air pressure in the respiratory organ, which is set as the starting value at the beginning of the inhalation phase, is established in accordance with the intrinsic PEEP. This advantageously allows a so-called auto-PEEP-controlled respiration support of the living being.

According to an advantageous refinement of the invention, the initial value of the air pressure in the respiratory organ is used as the basal pressure level, which the pressure level does not fall below at any time, the basal pressure level being established below the intrinsic PEEP by a pressure differential value. Upon a change of the intrinsic PEEP during respiration, the values in this regard are readjusted.

According to an advantageous refinement of the invention, a regulatory cycle of the air pressure in the respiratory organ comprises at least two respiration cycles, which immediately follow one another.

An advantageous ventilation device has at least one controllable air delivery unit, a pressure sensor for ascertaining the air pressure in the respiratory organ of a living being, and a programmable control unit. The programmable control unit is set up to execute a method of the previously described type, for example, by appropriate software programming. The ventilation device can advantageously additionally have one or more airflow meters, by which the airflow, which is supplied to and flows out of the air delivery unit and is modulated by the respiration of the patient, can be measured. The airflow meter can be implemented as a pneumotachograph, for example. The controllable air delivery unit can have a controllable turbine or an air compression apparatus, e.g., a piston compressor, for example. The air delivery unit can additionally have a pressure control valve or a valve configuration for controlling the output air quantity.

An advantageous valve control device can be connected as an auxiliary unit between a conventional ventilation device and the living being to be ventilated. The valve control device advantageously has at least one airflow meter, e.g., a pneumotachograph, a pressure sensor for ascertaining the air pressure in the respiratory organ of the living being, and at least one pressure control valve and one programmablem control unit. The programmable control unit is advantageously set up to execute a method according to at least one of the preceding claims, e.g., by corresponding software programming. A comparatively cost-effectively producible valve control device can thus be used as a supplement if a ventilation device is provided. The valve control device does not require a separate air delivery unit.

The invention is advantageously suitable for both invasive and also noninvasive ventilation.

An external respiration pressure is dynamically regulated by the invention, which is adapted to the respiration of the living being. A basal pressure level can advantageously be set approximately to values somewhat less than the patient-related intrinsic PEEP. The respiration support during the inhalation is performed by an inspiration-controlled pressure increase, e.g., in the magnitude of 2 to 30 mbar, which is set as a function of the illness of the particular patient and the volume flow resulting therefrom. In an advantageous embodiment, the pressure increase is regulated back to the basal pressure level as soon as the maximum inhalation speed is reached. In this way, it is ensured that hyperinflation of the lungs does not occur and the pressure support represents a work support for the inspirational musculature.

During the exhalation phase, a dynamic counter pressure is applied, which has the object of preventing the collapse of the "small airways", which are frequently affected particularly strongly by the illness, as long as possible and keeping them open as long as possible, wide enough that as much air as possible can still be exhaled from these downstream pulmonary alveoli. This results in better deflation of the lungs, as a result of which better gas exchange occurs. This in turn allows a subsequent inspiration having a greater tidal volume, which can in turn be used as a regulating variable for future respiration support.

The increase of the expirational pressure increase can be performed until a further increase of the expirational pressure no longer results in an increase of the inspirational tidal volume.

The invention is explained in greater detail hereafter on the basis of exemplary embodiments with the use of drawings.

BRIEF DESCRIPTION OF THE DRAWINGS

In the FIGS.

FIG. 2 shows a first embodiment of a ventilation cycle and

FIG. 3 shows further advantageous embodiments of ventilation cycles and

FIG. 4 shows a further advantageous embodiment of a ventilation cycle and

DETAILED DESCRIPTION THE INVENTION

Figure 1:
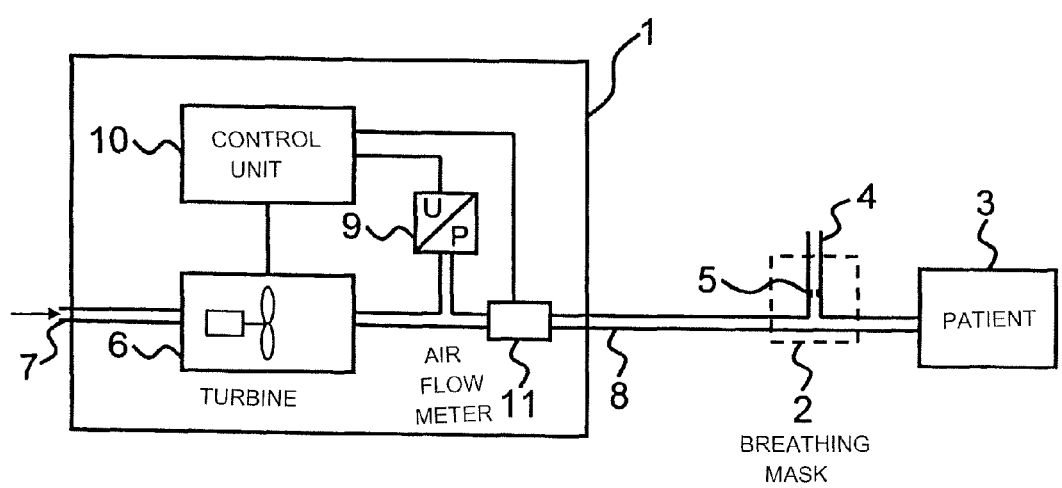
FIG. 1 shows a ventilation device in schematic illustration.

FIG. 1 shows a ventilation device 1, which is connected via a hose 8 to a breathing mask 2 or another suitable interface. The breathing mask 2 is connected to the mouth and/or nose or to deeper airways of a living being, or patient, 3. The breathing mask 2 has an outlet 4, which is open to the atmosphere, and which is connected to the hose 8 via a throttle point 5. A defined leakage is provided in the breathing mask 2 in this way.

The ventilation device 1 has a controllable turbine 6 having integrated pneumotachographic measuring configuration for the volume flow measurement and a pressure sensor 9, which is situated on the output side of the turbine 6 and is connected to the compressed air hose 8. Alternatively or additionally to the integrated pneumotachographic measuring configuration, an airflow meter 11 can also be provided. The pressure sensor 9, the airflow meter 11, and the turbine 6 are connected via electrical lines to an electronic control unit 10. The electronic control unit 10 receives a signal indicating the pressure in the compressed air hose 8 from the pressure sensor 9 and, from the turbine 6, receives a signal output from its pneumotachographic measuring configuration, which indicates the airflow pumped by the turbine 6 into the compressed air hose 8. The electronic control unit 10 can also receive a signal indicating the volume flow through the compressed air hose 8 from the optional airflow meter 11. The electronic control unit 10 analyzes the received signals and determines on the basis of the signals, using the flow resistance of the hose 8 known to the electronic control unit 10 and the known leakage of the breathing mask 2, the airflow flowing into the living being 3 and/or the airflow flowing out of the living being 3. In addition, the electronic control unit 10 determines the pressure existing in the respiratory organ of the living being 3 on the basis of the signals.

The electronic control unit 10 controls the turbine 6 and/or corresponding pressure control valves according to the previously described method. Air is sucked in via the turbine 6 by an air inlet 7 connected to the atmosphere and is discharged appropriately compressed via the hose 8 to the breathing mask 2 and thus to the living being 3.

FIG. 2 shows a first example of advantageous time curves of the airflow, shown by a volume flow $\dot{v}$, and the pressure p. In FIG. 2a, the airflow $\dot{v}$ is shown in idealized form in a healthy living being. In an inhalation phase between the points in time $t_1$ and $t_3$, the inhalation occurs, shown by an airflow curve 20. In an exhalation phase between the points in time $t_3$ and $t_4$, the exhalation occurs, shown by an airflow curve 21. FIG. 2b shows a pressure curve 22 running approximately in an inverse parabola in a time range between the points in time $t_1$ and $t_3$. The pressure p is increased from a neutral level, the basal pressure level $p_o$, to a maximum value between the points in time $t_1$ and $t_2$. The pressure p is regulated back to the basal pressure level between the points in time $t_2$ and $t_3$. After the point in time $t_3$, the pressure p is raised according to the curved section 23, the maximum value of the curved section 23 being reached relatively early during the exhalation phase and the pressure being lowered back to the basal pressure level $p_0$ accordingly at point in time $t_4$.

FIG. 3 shows further advantageous embodiments of pressure curves p for implementing the described invention (FIG. 3b), which are shown chronologically in relation to respiration cycles (airflow $\dot{v}$ in FIG. 3a). The areas shown shaded in FIG. 3b indicate the possible variation ranges of the curve sections 22, 23, within which the invention can be advantageously implemented.

In the pressure curves 30 through 33, the air pressure is raised during the respiration of the living being at specific times of the respiration cycle from a starting value and lowered again with progressing respiration of the living being so that, during an exhalation of the living being, there is always an air pressure in the respiratory organ of the living being which is higher than the starting value.

In the pressure curves 30 through 33, it is provided that the air pressure in the respiratory organ of the living being is firstly raised to a predetermined amount in an inhalation phase and then varied over the curve of the respiration cycle between this predetermined amount and the starting value and is lowered back to an initial value, which was set as the starting value at the beginning of the inhalation phase, at the end of an exhalation phase.

The pressure curve 34 corresponds to FIG. 2 and is only shown for comparative purposes in FIG. 3.

The pressure curves 35 through 38 show examples in which the air pressure in the respiratory organ of the living being is initially raised in an exhalation phase and then varied over the curve of the respiration cycle between a predetermined amount and the starting value and is lowered back to an initial value, which was set as the starting value at the beginning of the exhalation phase, during an inhalation phase.

The pressure curve 30 additionally shows an example in which the air pressure is initially raised to a predetermined amount in the respiratory organ of the living being in an inhalation phase, then remains at this predetermined amount over the curve of the inhalation, and is lowered back continuously at the beginning of the exhalation, initially slowly and then more rapidly, at the end of the exhalation phase to an initial value, which was set at the beginning of the inhalation phase as the starting value.

The pressure curve 31 shows an example of how the air pressure in the respiratory organ of the living being is initially raised to a predetermined amount in an inhalation phase, then remains at this predetermined amount over the curve of the inhalation, and is initially lowered rapidly by a specific amount at the beginning of the exhalation and is then lowered again continuously, initially slowly and then more rapidly, at the end of the exhalation phase to an initial value, which was set at the beginning of the inhalation phase as the starting value.

The pressure curve 32 shows an example of how the air pressure in the respiratory organ of the living being is initially raised to a predetermined amount in an inhalation phase, then remains at this predetermined amount up to the point in time of the maximum inhalation air flow, and is then lowered rapidly by a specific amount up to the beginning of the exhalation and is then again lowered continuously, initially slowly and then more rapidly, at the end of the exhalation phase to an initial value, which was set as the starting value at the beginning of the inhalation phase.

FIG. 4 shows a pressure curve which spans multiple respiration cycles (FIG. 4b), again shown in relation to the airflow $\dot{v}$ of normal respiration cycles (FIG. 4a). As shown on the basis of the curves 41, 42, the ventilation cycle of the ventilation device can comprise two respiration cycles of the living being. The curve 40 in FIG. 4b shows one ventilation cycle of the ventilation device, which comprises four respiration cycles of the living being. Furthermore, it is recognizable that the air pressure in the respiratory organ of the living being is raised at a predetermined point in time of a respiration cycle, then rises varying between a predetermined amount and the starting value over the curve of one or more respiration cycles, and is then lowered varying back to an initial value, which was set at the beginning of the pressure increase as the starting value, over the course of one or more respiration cycles again.

Figure 5:
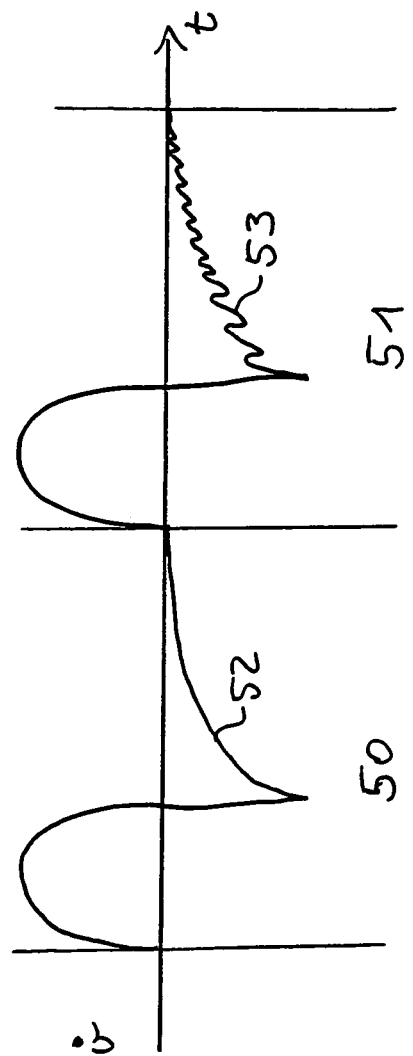
FIG. 5 shows a ventilation cycle with recognition of a superimposed oscillation.

FIG. 5 shows a curve 52 of the airflow $\dot{v}$, which is provided in a healthy living being, in a time range 50. A curve 53 is shown in a time range 51, in which a superimposed, higher-frequency oscillation can be established in the airflow $\dot{v}$ during the exhalation phase. This oscillation can be detected by the electronic control unit 10 and used as a control criterion for the controller of the ventilation.

The invention claimed is:

1. Method for the ventilation of a living being, performed by a ventilation device, comprising the steps of:
   detecting a respiration airflow ($\dot{v}$) flowing into the living being and out of the living being,
   ascertaining from the detected respiration airflow ($\dot{v}$) whether an inhalation phase or an exhalation phase is present,
   regulating an air pressure (p) in a respiratory organ of the living being,
   wherein, upon recognition of an inhalation phase in the step of ascertaining, initially raising the air pressure (p) in the respiratory organ at the beginning of the inhalation phase from an initial value of the air pressure (p), which was set at the beginning of the inhalation phase as the starting value (Po), to a predetermined amount, maintaining the air pressure (p) at said predetermined amount during the inhalation phase and into the exhalation phase, and then lowering the air pressure (p) at the end of the exhalation phase to the starting value (Po) and wherein upon recognition of an exhalation phase in the step of ascertaining, raising the air pressure (p) in the respiratory organ at the beginning of the exhalation phase.

2. Method according to claim 1, further comprising the step of increasing the air pressure (p) in the respiratory organ in the exhalation phase to a maximum pressure.

3. Method according to claim 1, further comprising the step of reducing the air pressure (p) in the respiratory organ in the exhalation phase at the end of the exhalation phase according to an essentially exponential decay function.

4. Method according to claim 1, wherein the air pressure (p) in the respiratory organ is only regulated at the beginning of the exhalation phase as detected in the step of ascertaining so that the respiration airflow ($\dot{v}$) flowing out of the living being reaches a predetermined amount.

5. Method according to claim 1, wherein, in the exhalation phase as detected in the step of ascertaining, the air pressure (p) in the respiratory organ is regulated in proportion to the respiration airflow ($\dot{v}$) of the exhalation.

6. Method according to claim 1, wherein tidal volume is ascertained from the detected respiration airflow, further comprising the steps of: increasing the maximum value and/or the pressure level of the air pressure (p) in the respiratory organ in the exhalation phase and/or a pressure curve is adapted if an increase of the tidal volume is established in preceding respiration cycles.

7. Method according to claim 6, wherein the increase of the maximum value and/or the pressure level of the air pressure (p) in the respiratory element in the exhalation phase is limited to a highest value.

8. Method according to claim 1, further comprising the steps of:
    ascertaining the respiration frequency, and
    increasing the maximum value and/or pressure level of the air pressure (p) in the respiratory organ in the exhalation phase, or
    adapting the pressure curve if a reduction of the respiratory frequency is established in preceding respiration cycles.

9. Method according to claim 1, further comprising the steps of:
    monitoring a time curve of the air pressure (p) and/or the respiration airflow ($\dot{v}$) in the respiratory organ for an occurrence of a superimposed oscillation having higher frequency than the respiration frequency, and
    increasing the maximum value and/or the pressure level of the air pressure (p) in the respiratory organ in the exhalation phase, or
    adapting the pressure curve if a superimposed oscillation is recognized.

10. Method according to claim 1, further comprising the step of ascertaining an intrinsic PEEP (Positive End Expiratory Pressure-pressure level at the end of the exhalation phase) of the living being from the detected respiration airflow ($\dot{v}$) as a function of the pressure increase in the exhalation phase and the initial value of the air pressure in the respiratory organ (Po), is established in accordance with the intrinsic PEEP.

11. Method according to claim 10, further comprising the step of using the initial value of the air pressure in the respiratory organ as the basal pressure level (pa), which the pressure level does not fall below at any time, a basal pressure level (Po) being established as less than the intrinsic PEEP by a pressure differential value.

12. Method according to claim 1, wherein a regulatory cycle of the air pressure (p) in the respiratory organ comprises at least two respiration cycles, a respiration cycle comprising an inhalation phase and an exhalation phase, which directly follow one another.

13. Ventilation device comprising:
    at least one controllable air delivery unit,
    at least one airflow meter,
    at least one pressure sensor, and
    at least one programmable control unit receiving inputs from the airflow meter and the pressure sensor, the programmable control unit being set up to control the air delivery unit by
    detecting a respiration airflow ($\dot{v}$) flowing into the living being and out of the living being,
    ascertaining from the detected respiration airflow ($\dot{v}$) whether an inhalation phase or an exhalation phase is present,
    regulating an air pressure (p) in a respiratory organ of the living being,
    wherein, upon recognition of an inhalation phase in the step of ascertaining, initially raising the air pressure (p) in the respiratory organ at the beginning of the inhalation from an initial value of the air pressure (p), which was set at the beginning of the inhalation phase as the starting value (Po), to a predetermined amount, maintaining the air pressure (p) at said predetermined amount during the inhalation phase and into the exhalation phase, and then lowering the air pressure (p) at the end of the exhalation phase to the starting value (Po) and wherein upon recognition of an exhalation phase in the step of ascertaining, raising the air pressure (p) in the respiratory organ at the beginning of the exhalation phase.

14. Valve control unit comprising:
    at least one pressure control valve,
    at least one airflow meter,
    at least one pressure sensor, and
    at least one programmable control unit receiving inputs from the airflow meter and the pressure sensor, the programmable control unit being set up to control an air delivery unit by
    detecting a respiration airflow ($\dot{v}$) flowing into the living being and out of the living being,
    ascertaining from the detected respiration airflow ($\dot{v}$) whether an inhalation phase or an exhalation phase is present,
    regulating an air pressure (p) in a respiratory organ of the living being,
    wherein, upon recognition of an inhalation phase in the step of ascertaining, initially raising the air pressure (p) in the respiratory organ at the beginning of the inhalation phase from an initial value of the air pressure (p), which was set at the beginning of the inhalation phase as the starting value (Po), to a predetermined amount, maintaining the air pressure (p) at said predetermined amount during the inhalation phase and into the exhalation phase, and then lowering the air pressure (p) at the end of the exhalation phase to the starting value (Po) and wherein upon recognition of an exhalation phase in the step of ascertaining, raising the air pressure (p) in the respiratory organ at the beginning of the exhalation phase.

15. Method for the ventilation of a living being performed by a ventilation device, comprising the steps of:

detecting a respiration airflow (v̇) flowing into the living being and out of the living being, ascertaining from the detected respiration airflow (v̇) whether an inhalation phase or an exhalation phase is provided, regulating an air pressure (p) in a respiratory organ of the living being, wherein, upon detecting the exhalation phase in the step of ascertaining, regulating the air pressure (p) in the respiratory organ in accordance with the respiration airflow (v̇) of the exhalation or parameters derived therefrom so that the respiration airflow flowing out of the living being reaches a predetermined amount, and upon recognition of an exhalation phase in the step of ascertaining, raising the air pressure (p) in the respiratory organ at the beginning of the exhalation phase by applying a dynamically controlled counter pressure against the respiration airflow flowing out of the living being to increase a dynamic lung resistance in the living being.

16. Method according to claim 15, further comprising the step of increasing the air pressure (p) in the respiratory organ in the exhalation phase to a maximum pressure.

17. Method according to claim 15, further comprising the step of reducing the air pressure (p) in the respiratory organ in the exhalation phase at the end of the exhalation phase according to an essentially exponential decay function.

18. Method according to claim 15, further comprising the step of, upon recognition of an exhalation phase in the step of ascertaining, raising the air pressure (p) in the respiratory organ at the beginning of the exhalation phase.

19. Method according to claim 18, wherein the air pressure (p) in the respiratory organ is only regulated at the beginning of the exhalation phase as detected in the step of ascertaining so that the respiration airflow (v̇) flowing out of the living being reaches a predetermined amount.

20. Method according to claim 15, wherein, in the exhalation phase as detected in the step of ascertaining, the air pressure (p) in the respiratory organ is regulated in proportion to the respiration airflow (v̇) of the exhalation.

21. Method according to claim 15, wherein tidal volume is ascertained from the detected respiration airflow, further comprising the steps of: increasing the maximum value and/or the pressure level of the air pressure (p) in the respiratory organ in the exhalation phase and/or a pressure curve is adapted if an increase of the tidal volume is established in preceding respiration cycles.

22. Method according to claim 21, wherein the increase of the maximum value and/or the pressure level of the air pressure (p) in the respiratory element in the exhalation phase is limited to a highest value.

23. Method according to claim 15, further comprising the steps of:
ascertaining the respiration frequency, and
increasing the maximum value and/or pressure level of the air pressure (p) in the respiratory organ in the exhalation phase, or
adapting the pressure curve if a reduction of the respiratory frequency is established in preceding respiration cycles.

24. Method according to claim 15, further comprising the steps of:
monitoring a time curve of the air pressure (p) and/or the respiration airflow (v̇) in the respiratory organ for an occurrence of a superimposed oscillation having higher frequency than the respiration frequency, and
increasing the maximum value and/or the pressure level of the air pressure (p) in the respiratory organ in the exhalation phase, or
adapting the pressure curve if a superimposed oscillation is recognized.

25. Method according to claim 15, further comprising the step of ascertaining an intrinsic PEEP (Positive End Expiratory Pressure-pressure level at the end of the exhalation phase) of the living being from the detected respiration airflow (v̇) as a function of the pressure increase in the exhalation phase and the initial value of the air pressure in the respiratory organ (Po), is established in accordance with the intrinsic PEEP.

26. Method according to claim 25, further comprising the step of using the initial value of the air pressure in the respiratory organ as the basal pressure level (pa), which the pressure level does not fall below at any time, a basal pressure level (Po) being established as less than the intrinsic PEEP by a pressure differential value.

27. Method according to claim 15, wherein a regulatory cycle of the air pressure (p) in the respiratory organ comprises at least two respiration cycles, a respiration cycle comprising an inhalation phase and an exhalation phase, which directly follow one another.

* * * * *